United States Patent [19]
Mashal et al.

[11] Patent Number: 5,824,471
[45] Date of Patent: Oct. 20, 1998

[54] DETECTION OF MISMATCHES BY CLEAVAGE OF NUCLEIC ACID HETERODUPLEXES

[75] Inventors: Robert Mashal, Brookline; Jeffrey Sklar, Chestnut Hill; Richard Kolodner, Jamaica Plain, all of Mass.

[73] Assignees: Brigham and Women's Hospital; Dana-Farber Cancer Institute, both of Boston, Mass.

[21] Appl. No.: 460,899

[22] Filed: Jun. 5, 1995

[51] Int. Cl.$^6$ ............................................. C12Q 1/68
[52] U.S. Cl. .................... 435/6; 935/77; 935/78; 435/196
[58] Field of Search ................. 435/6, 91.2, 183, 435/195, 196; 536/23.1; 935/77, 78

[56] References Cited

U.S. PATENT DOCUMENTS

| | | | |
|---|---|---|---|
| 4,988,617 | 1/1991 | Landegren et al. | 435/6 |
| 5,217,863 | 6/1993 | Cotton et al. | 435/6 |
| 5,459,039 | 10/1995 | Modrich et al. | 435/6 |

FOREIGN PATENT DOCUMENTS

WO 95/29251  11/1995  WIPO.

OTHER PUBLICATIONS

Dean (1995) *Nature Genetics* 9:103–4.
Stark (1991) *EMBO J.* 10:3541–8.
Forrest et al. (1995) *Nat. Genet.* 10:375–6.
Mashal et al. (1995) *Nat. Genet.* 9:177–83.
Kwiatkowski et al. (1994) *Nucl. Acids Res.* 22:2604–11.
Benson and West (1994) *J. Biol. Chem.* 269:5195–201.
Dodgson and Wells (1977) *Biochemistry* 16:2374–79.
Clazone et al. (1987) *Methods Enzymol.* 152:611–14.
Bertrand–Burggraf et al. (1994) *Mutation Res. DNA Rep.* 314:287–95.
Shenk et al. (1975) *Proc. Natl. Acad. Sci. USA* 72:989–993.
Bhattacharyya et al. (1991) "Model for the Interaction of DNA Junctions and Resolving Enzymes" *J. Mol. Biol.* 221:1191–1207.
Cotton, R.G. (1993) "Current Methods of Mutation Detection" *Mutat. Res.* 285, 125–144.
Chang, Dau–Yin and A–Lien Lu (1991) "Base mismatch-specific endonuclease activity in extracts from Saccharomyces cerevisiae" *Nucleic Acids Research* 19(17):4761–4766.
Davidow, L.S, (1992) "Selecting PCR designed mismatch primers to create diagnostic restrictions sites" *Comp. Appl. Biosci.* 8(2):193–194.
Don et al. (1991) "Touchdown PCR to circumvent spurious priming during gene amplification" *Nucl. Acids Res.* 19(4):4008.
Ellis et al. (1994) "MutS binding Protects heteroduplex DNA from exonuclease digestion in vitro: a simple method for detecting mutations" *Nucleic Acids Research* 22(13):2710–11.

Ganguly, A and D.J. Prockop (1990) "Detection of single–base mutations by reaction of DNA heteroduplexes with a water–soluble carbodiimide followed by primer extension: application to products from the polymerase chain reaction" *Nucl. Acids Res.* 18:3933–3839.
Ganguly et al. (1993) "Conformation–Sensitive Gel Electrophoresis for rapid detection of single–base differences in double–stranded PCR products and DNA fragments: Evidence for solvent–induced bends in DNA heteroduplexes" *Proc. Natl. Acad. Sci. USA* 90:10325–10329.
Groden et al. (1991) "Identification and characterization of the familial adenomatous polyposis coli gene" *Cell* 66:586–600.
Grompe, M. (1993) "The rapid detection of unknown mutations in nucleic acids" *Nature Genetics* 5:111–117.
Hyde et al. (1994) "Resolution of Recombination Intermediates by a Mammalian Activity Functionally Analogous to Escherichia coli RuvC Resolvase" *J. of Biological Chemistry* 269(7):5202–5209.
Jiricny et al. (1986) "Mismatch containing oligonucleotides bound by the E. Coli mut–S–encoded protein" *Nucl. Acids Res.* 16:7843–7853.
Kemper, B. and M. Garabett (1981) "Studies on T4–head maturation 1. Purification and characterization of gene–49–controlled endonuclease" *Eur. J. Biochem.* 115:123–131.
Kosak, and B.W. Kemper (1990) "Large Scale Preparation of T4 Endonuclease VII from over–expressing Bacteria" *J. Biochem.* 194:799–784.
Lishanski et al. (1994) "Mutation detection by mismatch binding protein, MutS, in amplified DNA: Application to the cystic fibrosis gene" *Proc. Natl. Acad. Sci. USA* 91:2674–2678.
Lu et al. (1991) "Resolution of Branched DNA Substrates by T7 Endonuclease I and Its Inhibition" *J. of Biological Chemistry* 266(4):2531–2536.
Lu A–Lien and Ih–Chang Hsu (1992) "Detection of Single DNA Base Mutations With Mismatch Repair Enzymes" *Genomics* 14:249–255.
Myers et al. (1985) "Detection of single base substitutions by ribonuclease cleavage at mismatches in RNA:DNA duplexes" *Science* 230: 1242–1246.
Myers et al. (1987) "Detection and Localization of Single Base Change by Denaturing Gradient Gel Electrophoresis" *Methods in Enzymology* 155:501–527.
Nelson et al. (1993) "Genomic Mismatch scanning: A new approach to genetic linkage mapping" *Nature Genetics* 4:11–18.

(List continued on next page.)

*Primary Examiner*—W. Gary Jones
*Assistant Examiner*—Amy Atzel
*Attorney, Agent, or Firm*—Lahive & Cockfield, LLP

[57] ABSTRACT

Novel methods and kits for detecting mismatches in nucleic acids using one or more resolvase enzymes. These methods can be used in medical procedures or research, veterinary procedures or research, agricultural applications, forensics, and paternity testing. For example, in forensics and paternity testing, methods of the invention can replace or complement RFLP mapping.

30 Claims, No Drawings

OTHER PUBLICATIONS

Orita et al. (1989) "Rapid and sensitive detection of point mutations and DNA polymorphism's using the polymarase chain reaction" *Genomics* 5:874–879.

Picksley et al. (1990) "Cleavage Specificity of Bacteriophage T4 Endonuclease VII and Bacteriophage T7 Endonuclease I on Synthetic Branch Migratable Holliday Junction" *J. Mol. Bio.* 212:723–735.

Pottmeyer, S. and K. Börries (1992) "T4 Endonuclease VII Resolves Cruciform DNA with Nick and Counter–Nick and Its Activity is Directed by Local Nucleotide Sequence" *J. of Mol. Biology* 220:607–615.

Shenk et al (1975) "Mapping of mutational alterations in DNA with $S_1$ nuclease: the location of deletion, insertions and temperature–sensitive mutations in SV40" *Cold Spring Harb. Symp. Quant. Biol.* 1:61:67.

Sharples et al. (1984) "Processing of Intermediates in Recombination and DNA repair: identification of a new endonuclease that specifically cleaves Holliday junctions" *The EMBO Journal* 13(24):6133–6142.

Smooker P.M. and R.G.H. Cotton, (1993) "The use of chemical reagents in the detection of DNA mutations" *Mutat. Res.* 288:65–77.

Solaro et al. (1993) "Endonuclease VII of Phage T4 Triggers Mismatch Correction in Vitro" *J. of Molec. Biol.* 230:868–877.

Verpy et al. (1994) "Efficient detection of point mutations on color–coded strands of target DNA" *Proc. Natn. Acad. Sci. U.S.A.* 91:1873–1877.

Villarejo, M.R. and I. Zabin (1974) "Beta–galactosidase from termination and deletion mutant strains" *J. Bacteriology,* 120:466–474.

White et al. (1992) "Detecting Single Base Substitutions as Heteroduplex Polymorphisms" *Genomics* 12:301:306.

Yeh et al. (1991) "Two Nicking Enzyme Systems Specific for Mismatch–Containing DNA in Nuclear Extracts from Human Cells" *J. of Biological Chemistry* 266(10):6480–6484.

Youil et al. (1993) "Screening for Mutations by Enzyme Cleavage of Mismatch using T4 Endonuclease VII" *The American Journal of Human Genetics* vol. 53(3) Abstract 1257.

Youll et al. (1994) "Screening of 66 Mouse β–globin promoter mutations using Enzyme Mismatch Cleavage" *The American Journal of Human Genetics* (3) abstract 1468.

DETECTION OF MISMATCHES BY CLEAVAGE OF NUCLEIC ACID HETERODUPLEXES

BACKGROUND OF THE INVENTION

The invention relates to the detection of mismatches in nucleic acids, e.g., the detection of mutations in DNA.

Work described herein was supported by grants K11 CA01556 and P20 CA58203 from NIH. The government has certain rights in the invention.

Efficient detection of mutations in genomic DNA is a matter of recurring interest in genetics and oncology. Many procedures have been applied to this problem with varying degrees of success.

Rapid screening techniques for detecting point mutations within DNA have generally relied on one of two principles. One group of techniques has used conformational changes in DNA fragments created by sequence heterogeneity. These conformational changes can result in altered electrophoretic mobility of a fragment when assayed under appropriate conditions. The three most widely used procedures for detecting these changes in electrophoretic mobility are denaturing gradient gel electrophoresis (DGGE) (Myers, et al. (1987) *Meth. Enzym.* 155, 501–527), single-stranded conformational polymorphism (SSCP) analysis (Orita, et al. (1989) *Genomics* 4, 874–879) and heteroduplex analysis (HA) in standard or modified gel matrices (White, et al. (1992) *Genomics* 5, 301–306). While these techniques are relatively rapid and easy to use, they can frequently suffer from one or more of the following drawbacks: not all sequence changes result in conformational differences which can always be detected; the optimal conditions for the assay often vary with each DNA fragment; the sensitivity of these techniques often decreases with increasing size of the DNA fragment being screened; and generally no information is obtained about the nature or location of the mutation. An alternative method involving conformation-sensitive gel electrophoresis in partially denaturing solvents has been described and is reported to detect many mutations even in relatively large fragments of DNA (up to 800 base pairs) (Ganguly, et al. (1993) *Proc. Natl. Acad. Sci. USA.* 90, 10325–10329).

A second group of techniques has relied on the ability of proteins or chemicals to recognize DNA at the site of sequence mismatch within heteroduplexes. The major advantage of these techniques over those which exploit conformational differences is that they potentially provide information about the location of the mutation. Early techniques of this type utilized single-strand-specific endonucleases such as $S_1$ and mung bean nucleases to digest DNA at sites of unpaired sequence (Shenk, et al. (1975) *Cold Spring Harb. Symp. Quant. Biol.* 1, 61–67). The usefulness of these enzymes was hampered by the declining sensitivity of the enzyme as the length of the mismatched sequence decreased and the strong effect of sequence context on the efficiency of digestion at sites of small mismatches. More recently, RNAse A was applied to digest mismatched RNA in RNA:DNA heteroduplexes, a technique termed RNAse protection (Myers, et al. (1985) *Science* 230, 1242–1248). A disadvantage of this technique is the inconvenience of RNA as a substrate, both in terms of its inherent instability and the need to either isolate RNA from a tissue in which the specific gene is expressed or to prepare an RNA probe. Furthermore, in many cases, only about 50% of all single base mismatches are cut by RNAse A.

Chemical mismatch cleavage (CMC) is highly specific and can be applied to relatively large DNA fragments (Smooker, et al. (1993) *Mutat. Res.* 288, 65–77). One drawback of CMC is that it often requires the use of highly mutagenic or explosive compounds. A variation of this technique, which utilizes carbodiimide to cleave mismatched DNA, may be less specific compared to other methods, although its specificity is difficult to assess due to the limited application it has received to date (Ganguly and Prockop (1990) *Nucl. Acids Res.* 18, 3933–3939).

SUMMARY OF THE INVENTION

In one aspect, the invention features a method of detecting a mismatch between a first nucleic acid strand and a second nucleic acid strand including: (i) forming a plurality of duplexes, each duplex including a molecule of the first nucleic acid strand, or a portion thereof, and a molecule of the second nucleic acid strand, or a portion thereof; (ii) contacting a first mismatch cleavage enzyme, e.g., a first resolvase, and a second mismatch cleavage enzyme, e.g., a second resolvase, with the plurality of duplexes; (iii) determining if a duplex is cleaved by a mismatch cleavage enzyme, e.g., a resolvase, cleavage being indicative of a mismatch.

In another aspect, the invention features a method of detecting a mismatch between a first nucleic acid strand and a second nucleic acid strand including: (i) forming a first duplex between a molecule of the first strand, or a portion thereof, and a molecule of the second strand, or a portion thereof; (ii) contacting the first duplex with a first mismatch cleavage enzyme, e.g., a first resolvase; (iii) forming a second duplex between a molecule of the first and a molecule of the second strand; (iv) contacting the second duplex with a second mismatch cleavage enzyme, e.g., a second resolvase; (v) determining if at least one strand of the first strand or the second duplex is cleaved, cleavage being indicative of a mismatch. (The order and numbering of the steps in the methods described herein are not meant to imply that the steps of any method described herein must be performed in the order in which the steps are listed or in the order in which the steps are numbered. The steps of any method disclosed herein can be performed in any order which results in a functional method.)

In another aspect, the invention features a method of detecting a mismatch between a first nucleic acid strand and a second nucleic acid strand including: (i) amplifying all or a portion of the first strand; (ii) amplifying all or a portion of the second strand; (iii) forming a first duplex between an amplification product of the first strand and an amplification product of the second strand; (iv) forming a second duplex between an amplification product of the first strand and an amplification product of the second strand; (v) contacting the first duplex with a first mismatch cleavage enzyme, e.g., a first resolvase; (vi) contacting the second duplex with a second mismatch cleavage enzyme, e.g., a second resolvase; (vii) determining if at least one strand of the duplex is cleaved, cleavage being indicative of a mismatch.

In another aspect, the invention features a method of detecting a mismatch between a first nucleic acid strand and a second nucleic acid strand including: (i) amplifying all or a portion of the first strand; (ii) providing a plurality of the second strands; (iii) forming a first duplex between an amplification product of the first strand and one of the second strands; (iv) forming a second duplex between an amplification product of the first strand and one of the second strands; (v) contacting the first duplex with a first mismatch cleavage enzyme, e.g., a first resolvase; (vi) contacting the second duplex with a second mismatch cleavage enzyme, e.g., a second resolvase; (vii) determining if at least one strand of the duplex is cleaved, cleavage being indicative of a mismatch.

In yet another aspect, the invention features a method of detecting a mismatch between a first nucleic acid strand and a second nucleic acid strand including: (i) forming a duplex between a molecule of the first strand, or a portion thereof, and the second strand, or a portion thereof; (ii) contacting the duplex with a first mismatch cleavage enzyme, e.g., a first resolvase; (iii) determining if at least one strand of the duplex is cleaved, cleavage being indicative of a mismatch, provided that at least one of the following conditions is met: the duplex is at least 30, 40, 50, 60 70, 80, 90, 100, or more base pairs in length; the first strand is human DNA; the resolvase is other than T4E7; the resolvase is T7E1.

In another aspect, the invention features a method of determining the location of a mismatch between a first nucleic acid strand and a second nucleic acid strand including: (i) forming a plurality of duplexes, each duplex including a molecule of the first nucleic acid strand, or a portion thereof, and a molecule of the second nucleic acid strand, or a portion thereof; (ii) contacting a first mismatch cleavage enzyme, e.g., a first resolvase, and a second mismatch cleavage enzyme, e.g., a second resolvase, with the plurality of duplexes; (iii) determining the distance between the cleavage site and a second site on the strand (or the complement of the strand). The distance between the cleavage site and a second site on a strand can be determined by several methods known to those skilled in the art. For example, the cleaved strand can be radiolabeled at one end and electrophoresed on a gel, e.g., a polyacrylamide gel, along with one or more molecular weight standards. The size of the cleaved fragment indicates the distance between the cleavage site and the end of the molecule, which, e.g., in the case of an amplified fragment, will generally be known from the sequence of the primer.

In yet another aspect, the invention features a method of determining the location of a mismatch between a first nucleic acid strand and a second nucleic acid strand including: (i) forming a first duplex between a molecule of the first strand, or a portion thereof, and a molecule of the second strand, or a portion thereof; (ii) contacting the first duplex with a first mismatch cleavage enzyme, e.g., a first resolvase; (iii) forming a second duplex between a molecule of the first strand and a molecule of the second strand; (iv) contacting the second duplex with a second mismatch cleavage enzyme, e.g., a second resolvase; (v) determining the distance between the cleavage site and a second site on the strand (or the complement of the strand).

In another aspect, the invention features a method of determining the location of a mismatch between a first nucleic acid strand and a second nucleic acid strand including: (i) forming a duplex between a molecule of the first strand, or a portion thereof, and the second strand, or a portion thereof; (ii) contacting the duplex with a first mismatch cleavage enzyme, e.g., a first resolvase; (iii) determining the distance between the cleavage site and a second site on the strand (or the complement of the strand), provided that at least one of the following conditions is met: the duplex is at least 30, 40, 50, 60 70, 80, 90, 100, or more base pairs in length; the resolvase is other than T4E7; the resolvase is T7E1.

In another aspect, the invention features a reaction mixture, preferably an in vitro reaction mixture, used in a method of the invention.

In another aspect, the invention features a kit for evaluating a nucleic acid. The kit includes one or more of the following components: a first purified mismatch cleavage enzyme, e.g., a first purified resolvase; a second purified mismatch cleavage enzyme, e.g., a second purified resolvase; a purified nucleic acid molecule, e.g., a primer, or a human DNA, or reference DNA used to form a duplex with a target DNA from the subject or sample; a reaction solution suitable for performing a cleavage reaction with the first resolvase; a reaction solution suitable for performing a cleavage reaction with the second resolvase; instructions for using the materials of the kit to test a subject or sample for the presence of a lesion.

In preferred embodiments the kit includes: a first primer, and a second primer, the first and second primers defining a region which includes a potential mismatch site in a preselected gene.

In preferred embodiments the kit includes: a human DNA, a first primer, and a second primer, the first and second primers.

In preferred embodiments the kit includes: a human DNA, a first primer, and a second primer, the first and second primers defining a region which includes potential mismatch site in a preselected gene and wherein the human DNA is wild-type at least one nucleotide in the region between said first and second primers.

In preferred embodiments one resolvase is T4E7 and the other is T7E1.

In preferred embodiments the kit includes a precast gel suitable for the analysis of nucleic acid samples.

The presence or stage of some disorders, e.g., some disorders characterized by unwanted cell proliferation, are correlated with the presence, in diseased tissue, of characteristic DNA lesions. For example, tissue from many cancers is often characterized by the presence of lesions in tumor suppressor genes. Methods of the invention, e.g., methods of the invention which can be used to detect the presence of a mismatch, can be used to evaluate the presence or stage of such a disorder in a subject, e.g., an experimental animal or a human. Methods of the invention can also be used to evaluate the efficacy of a treatment of such a disorder, where the efficacy of the treatment is correlated with the prevalence of a lesion in a tissue of the subject.

The invention can be used to evaluate the past exposure of a subject, e.g., an experimental animal or a human, to agents which result in damage to the subject's DNA. For example, methods of the invention, e.g., methods of the invention which can be used to detect the presence of a mismatch, can be used to evaluate the exposure of a subject to an environmental, occupational, or therapeutic agent which results in DNA lesions. Exposure is correlated with the existence of one or more lesions (which lesions can result in a mismatch) in the subject as measured, e.g., in a tissue sample from the subject.

The invention allows the rapid and efficient comparison of two nucleic acid sequences, preferably DNA sequences. A strand of the first nucleic acid sequence is hybridized to its complement from the second nucleic acid sequence. The presence of a mismatch (which can be detected by methods of the invention) is indicative of a difference in the two sequences.

Methods of the invention are useful for determining if there is a difference between two closely related nucleic acid sequences, e.g., between a target sequence, e.g., a histocompatibility gene from a patient, and a reference sequence, e.g., a characterized histocompatibility gene from a control. The method is particularly useful where there is no easily demonstrated difference in the restriction maps of the target and reference sequence. This method is useful, e.g., where the reference sequence is derived from the genome of a known pathogen and the target sequence is derived from a clinically isolated pathogen.

Methods of the invention can be used to make a rapid determination of whether prospective parents carry lesions in the same gene and can thus serve as a method of determining the risk of a birth defect in the offspring.

Methods of the invention can also be used to discover lesions associated with a disorder. A target of a strand of a nucleic acid from a subject, e.g., an experimental animal or a human, at risk for a disorder is hybridized to its complement from a reference nucleic acid, e.g., a strand nucleic acid from a subject not at risk for a disorder. Methods of the invention can be used to detect and locate lesions in the target strand.

Methods and reagents of the invention allow relatively rapid mutation detection, allow screening of large stretches of DNA with high sensitivity and specificity, do not involve expensive or elaborate instrumentation, do not require toxic or dangerous compounds, and provide information about the location and nature of the mutation. Methods of the invention can be used in medical procedures or research, veterinary procedures or research, agricultural applications, forensics, and paternity testing. For example, in forensics and paternity testing, methods of the invention can replace or complement RFLP mapping.

Other features and advantages of the invention will be apparent from the following description and from the claims.

DETAILED DESCRIPTION OF THE INVENTION

In one aspect, the invention features a method of detecting a mismatch between a first nucleic acid strand and a second nucleic acid strand including: (i) forming a plurality of duplexes, each duplex including a molecule of the first nucleic acid strand, or a portion thereof, and a molecule of the second nucleic acid strand, or a portion thereof; (ii) contacting a first mismatch cleavage enzyme, e.g., a first resolvase, and a second mismatch cleavage enzyme, e.g., a second resolvase, with the plurality of duplexes; (iii) determining if a duplex is cleaved by a mismatch cleavage enzyme, e.g., a resolvase, cleavage being indicative of a mismatch.

In another aspect, the invention features a method of detecting a mismatch between a first nucleic acid strand and a second nucleic acid strand including: (i) forming a first duplex between a molecule of the first strand, or a portion thereof, and a molecule of the second strand, or a portion thereof; (ii) contacting the first duplex with a first mismatch cleavage enzyme, e.g., a first resolvase; (iii) forming a second duplex between a molecule of the first and a molecule of the second strand; (iv) contacting the second duplex with a second mismatch cleavage enzyme, e.g., a second resolvase; (v) determining if at least one strand of the first strand or the second duplex is cleaved, cleavage being indicative of a mismatch. (The order and numbering of the steps in the methods described herein are not meant to imply that the steps of any method described herein must be performed in the order in which the steps are listed or in the order in which the steps are numbered. The steps of any method disclosed herein can be performed in any order which results in a functional method.)

The various steps or reactions of a method can be performed in the same reaction mix, e.g. in the same reaction vessel. However, as is discussed below, it is often desirable to perform steps of a method, e.g., the mismatch cleavage enzyme cleavage reactions, e.g., the resolvase cleavage reactions, separately. Thus, in embodiments wherein the first duplex and the second duplex are formed in the same reaction mixture: the first mismatch cleavage enzyme, e.g., the first resolvase, is contacted with the first duplex and the second mismatch cleavage enzyme, e.g., the second resolvase, is contacted with the second duplex in the same reaction mixture, or alternatively, the first mismatch cleavage enzyme, e.g., the first resolvase, is contacted with the first duplex in a first reaction mixture and the second mismatch cleavage enzyme, e.g., the second resolvase, is contacted with the second duplex in a second reaction mixture. In other preferred embodiments, the first duplex is formed in a first reaction mixture and the second duplex is formed in a second reaction mixture and the first mismatch cleavage enzyme, e.g., the first resolvase, is contacted with the first duplex in the first reaction mixture and the second mismatch cleavage enzyme, e.g., the second resolvase, is contacted with the second duplex in the second reaction mixture.

In the case of a subject or sample which is heterozygous for a site, e.g., a mutation of interest, the first and second strands can be derived from the subject or sample. Where a subject or sample is homozygous for a site of interest it will often be desirable to supply strands for duplex formation from another source. In preferred embodiments, the first strand is derived from a subject at risk for a mutation and the second strand has a wild-type sequence for the mutation and: the first strand encodes the sense or anti-sense strand of a mutant allele derived from a subject at risk for a mutation; the second strand is derived from the subject at risk for a mutation; the second strand encodes the sense or antisense strand of a wild type allele for the mutation; the second strand is not derived from the subject at risk for a mutation; the second strand is derived from a subject not at risk for a mutation or for a disorder associated with a mutation.

In preferred embodiments: the first resolvase is T4E7; the second resolvase is T7E1; the first resolvase is capable of cleaving at least one strand of a duplex having a mismatch in a mismatch-dependent fashion; the second resolvase is capable of cleaving at least one strand of a duplex having a mismatch in a mismatch-dependent fashion; the first resolvase and the second resolvase have different activities, e.g., they cleave at a particular mismatch with different efficiencies; the first resolvase cleaves a first preselected mismatch more efficiently than does the second resolvase; the second resolvase cleaves a second preselected mismatch more efficiently than does the first resolvase.

In preferred embodiments, the method further includes: providing a plurality of the first strand molecules, e.g., by amplifying all or a portion of the first strand; providing a plurality of the second strand molecules, e.g., by amplifying all or a portion of the second strand; providing a plurality of the first and the second strand molecules, e.g., by amplifying all or a portion of the first and the second strand.

In preferred embodiments: the first strand is DNA; the second strand is DNA.

In preferred embodiments: a mismatch is generated by a point mutation in the first strand or in the second strand; a mismatch is generated by a gross aberration in the first strand or in the second strand; a mismatch is generated by a deletion in the first strand or in the second strand; a mismatch is generated by an insertion in the first strand or in the second strand; the mismatch cleaved by the first or second resolvase is in any gene. For example, the mismatch can be in a gene which conditions cell proliferation, e.g., an oncogene, in a gene responsible for a congenital disorder, in a gene responsible for cell cycle regulation, or in a tumor suppressor gene. In another preferred embodiment, the mismatch can be in an extragenic region. In further preferred embodiments: the mismatch can be in one of the following genes: CFTR, APC, p53, Rb, BRCA1, HMSH1, or HMLH1.

In preferred embodiments the method includes: (i) amplifying all or a portion of the first strand; (ii) amplifying all or a portion of the second strand; (iii) forming a first duplex between an amplification product of the first strand and an amplification product of the second strand; (iv) forming a second duplex between an amplification product of the first strand and an amplification product of the second strand.

In preferred embodiments the method includes: (i) amplifying all or a portion of the first strand; (ii) providing a plurality of the second strands; (iii) forming a first duplex between an amplification product of the first strand and one of the second strands; (iv) forming a second duplex between an amplification product of the first strand and one of the second strands.

In another aspect, the invention features a method of detecting a mismatch between a first nucleic acid strand and a second nucleic acid strand including: (i) amplifying all or a portion of the first strand; (ii) amplifying all or a portion of the second strand; (iii) forming a first duplex between an amplification product of the first strand and an amplification product of the second strand; (iv) forming a second duplex between an amplification product of the first strand and an amplification product of the second strand; (v) contacting the first duplex with a first mismatch cleavage enzyme, e.g., a first resolvase; (vi) contacting the second duplex with a second mismatch cleavage enzyme, e.g., a second resolvase; (vii) determining if at least one strand of the duplex is cleaved, cleavage being indicative of a mismatch.

In another aspect, the invention features a method of detecting a mismatch between a first nucleic acid strand and a second nucleic acid strand including: (i) amplifying all or a portion of the first strand; (ii) providing a plurality of the second strands; (iii) forming a first duplex between an amplification product of the first strand and one of the second strands; (iv) forming a second duplex between an amplification product of the first strand and one of the second strands; (v) contacting the first duplex with a first mismatch cleavage enzyme, e.g., a first resolvase; (vi) contacting the second duplex with a second mismatch cleavage enzyme, e.g., a second resolvase; (vii) determining if at least one strand of the duplex is cleaved, cleavage being indicative of a mismatch.

In yet another aspect, the invention features a method of detecting a mismatch between a first nucleic acid strand and a second nucleic acid strand including: (i) forming a duplex between a molecule of the first strand, or a portion thereof, and the second strand, or a portion thereof; (ii) contacting the duplex with a first mismatch cleavage enzyme, e.g., a first resolvase; (iii) determining if at least one strand of the duplex is cleaved, cleavage being indicative of a mismatch, provided that at least one of the following conditions is met: the duplex is at least 30, 40, 50, 60 70, 80, 90, 100, or more base pairs in length; the first strand is human DNA; the resolvase is other than T4E7; the resolvase is T7E1.

In preferred embodiments, the first strand is derived from a subject at risk for a mutation and the second strand has a wild-type sequence for the mutation and: the first strand encodes the sense or anti-sense strand of a mutant allele derived from a subject at risk for a mutation; the second strand is derived from the subject at risk for a mutation; the second strand encodes the sense or antisense strand of a wild type allele for the mutation; the second strand is not derived from the subject at risk for a mutation; the second strand is derived from a subject not at risk for a mutation or for a disorder associated with a mutation.

In preferred embodiments: the resolvase is capable of cleaving at least one strand of a duplex having a mismatch in a mismatch-dependent fashion.

In preferred embodiments, the method further includes: providing a plurality of the first strand molecules, e.g., by amplifying all or a portion of the first strand; providing a plurality of the second strand molecules, e.g., by amplifying all or a portion of the second strand; providing a plurality of the first and the second strand molecules, e.g., by amplifying all or a portion of the first and the second strand.

In preferred embodiments: the first strand is DNA; the second strand is DNA.

In preferred embodiments: a mismatch is generated by a point mutation in the first strand or in the second strand; a mismatch is generated by a gross aberration in the first strand or in the second strand; a mismatch is generated by a deletion in the first strand or in the second strand; a mismatch is generated by an insertion in the first strand or in the second strand; the mismatch cleaved by the first or second resolvase is in any gene. For example, the mismatch can be in a gene which conditions cell proliferation, e.g., an oncogene, in a gene responsible for a congenital disorder, in a gene responsible for cell cycle regulation, or in a tumor suppressor gene. In another preferred embodiment, the mismatch can be in an extragenic region. In further preferred embodiments: the mismatch can be in one of the following genes: CFTR, APC, p53, Rb, BRCA1, HMSH1, or HMLH1.

In preferred embodiments, the method includes: (i) amplifying all or a portion of the first strand; (ii) amplifying all or a portion of the second strand; (iii) forming a duplex between an amplification product of the first strand and an amplification product of the second strand.

In other preferred embodiments, the method includes: (i) amplifying all or a portion of the first strand; (ii) providing a plurality of the second strands; (iii) forming a duplex between an amplification product of the first strand and one of the second strands.

In another aspect, the invention features a method of determining the location of a mismatch between a first nucleic acid strand and a second nucleic acid strand including: (i) forming a plurality of duplexes, each duplex including a molecule of the first nucleic acid strand, or a portion thereof, and a molecule of the second nucleic acid strand, or a portion thereof; (ii) contacting a first mismatch cleavage enzyme, e.g., a first resolvase, and a second mismatch cleavage enzyme, e.g., a second resolvase, with the plurality of duplexes; (iii) determining the distance between the cleavage site and a second site on the strand (or the complement of the strand). The distance between the cleavage site and a second site on a strand can be determined by several methods known to those skilled in the art. For example, the cleaved strand can be radiolabeled at one end and electrophoresed on a gel, e.g., a polyacrylamide gel, along with one or more molecular weight standards. The size of the cleaved fragment indicates the distance between the cleavage site and the end of the molecule, which, e.g., in the case of an amplified fragment, will generally be known from the sequence of the primer.

In yet another aspect, the invention features a method of determining the location of a mismatch between a first nucleic acid strand and a second nucleic acid strand including: (i) forming a first duplex between a molecule of the first strand, or a portion thereof, and a molecule of the second strand, or a portion thereof; (ii) contacting the first duplex with a first mismatch cleavage enzyme, e.g., a first resolvase; (iii) forming a second duplex between a molecule of the first strand and a molecule of the second strand; (iv) contacting the second duplex with a second mismatch cleavage enzyme, e.g., a second resolvase; (v) determining the distance between the cleavage site and a second site on the strand (or the complement of the strand).

In embodiments wherein the first duplex and the second duplex are formed in the same reaction mixture; the first mismatch cleavage enzyme, e.g., the first resolvase, is contacted with the first duplex and the second mismatch cleavage enzyme, e.g., the second resolvase, is contacted with the second duplex in the same reaction mixture, or alternatively the first mismatch cleavage enzyme, e.g., the first resolvase, is contacted with the first duplex in a first reaction mixture and the second mismatch cleavage enzyme, e.g., the second resolvase, is contacted with the second duplex in a second reaction mixture. In other preferred embodiments, the first duplex is formed in a first reaction mixture and the second duplex is formed in a second reaction mixture and the first mismatch cleavage enzyme, e.g., the first resolvase, is contacted with the first duplex in the first reaction mixture and the second mismatch cleavage enzyme, e.g., the second resolvase, is contacted with the second duplex in the second reaction mixture.

In preferred embodiments, the first strand is derived from a subject at risk for a mutation and the second strand has a wild-type sequence for the mutation and: the first strand encodes the sense or anti-sense strand of a mutant allele derived from a subject at risk for a mutation; the second strand is derived from the subject at risk for a mutation; the second strand encodes the sense or antisense strand of a wild type allele for the mutation; the second strand is not derived from the subject at risk for a mutation; the second strand is derived from a subject not at risk for a mutation or for a disorder associated with a mutation.

In preferred embodiments: the first resolvase is T4E7; the second resolvase is T7E1; the first resolvase is capable of cleaving at least one strand of a duplex having a mismatch in a mismatch-dependent fashion; the second resolvase is capable of cleaving at least one strand of a duplex having a mismatch in a mismatch-dependent fashion; the first resolvase and the second resolvase have different activities, e.g., they cleave at a particular mismatch with different efficiencies; the first resolvase cleaves a first preselected mismatch more efficiently than does the second resolvase; the second resolvase cleaves a second preselected mismatch more efficiently than does the first resolvase.

In preferred embodiments, the method further includes: providing a plurality of the first strand molecules, e.g., by amplifying all or a portion of the first strand; providing a plurality of the second strand molecules, e.g., by amplifying all or a portion of the second strand; providing a plurality of the first and the second strand molecules, e.g., by amplifying all or a portion of the first and the second strand.

In preferred embodiments: the first strand is DNA; the second strand is DNA.

In preferred embodiments: a mismatch is generated by a point mutation in the first strand or in the second strand; a mismatch is generated by a gross aberration in the first strand or in the second strand; a mismatch is generated by a deletion in the first strand or in the second strand; a mismatch is generated by an insertion in the first strand or in the second strand; the mismatch cleaved by the first or second resolvase is in any gene. For example, the mismatch can be in a gene which conditions cell proliferation, e.g., an oncogene, in a gene responsible for a congenital disorder, in a gene responsible for cell cycle regulation, or in a tumor suppressor gene. In another preferred embodiment, the mismatch can be in an extragenic region. In further preferred embodiments: the mismatch can be in one of the following genes: CFTR, APC, p53, Rb, BRCA1, HMSH1, or HMLH1.

In preferred embodiments, the method includes: (i) amplifying all or a portion of the first strand; (ii) amplifying all or a portion of the second strand; (iii) forming a first duplex between an amplification product of the first strand and an amplification product of the second strand; (iv) forming a second duplex between an amplification product of the first strand and an amplification product of the second strand.

In other preferred embodiments, the method includes: (i) amplifying all or a portion of the first strand; (ii) providing a plurality of the second strands; (iii) forming a first duplex between an amplification product of the first strand and one of the second strands; (iv) forming a second duplex between an amplification product of the first strand and one of the second strands.

In another aspect, the invention features a method of determining the location of a mismatch between a first nucleic acid strand and a second nucleic acid strand including: (i) forming a duplex between a molecule of the first strand, or a portion thereof, and the second strand, or a portion thereof; (ii) contacting the duplex with a first mismatch cleavage enzyme, e.g., a first resolvase; (iii) determining the distance between the cleavage site and a second site on the strand (or the complement of the strand), provided that at least one of the following conditions is met: the duplex is at least 30, 40, 50, 60 70, 80, 90, 100, or more base pairs in length; the resolvase is other than T4E7; the resolvase is T7E1.

In preferred embodiments, the first strand is derived from a subject at risk for a mutation and the second strand has a wild-type sequence for the mutation and: the first strand encodes the sense or anti-sense strand of a mutant allele derived from a subject at risk for a mutation; the second strand is derived from the subject at risk for a mutation; the second strand encodes the sense or antisense strand of a wild type allele for the mutation; the second strand is not derived from the subject at risk for a mutation; the second strand is derived from a subject not at risk for a mutation or for a disorder associated with a mutation.

In preferred embodiments: the resolvase is capable of cleaving at least one strand of a duplex having a mismatch in a mismatch-dependent fashion.

In preferred embodiments, the method further includes: providing a plurality of the first strand molecules, e.g., by amplifying all or a portion of the first strand; providing a plurality of the second strand molecules, e.g., by amplifying all or a portion of the second strand; providing a plurality of the first and the second strand molecules, e.g., by amplifying a portion of the first and the second strand.

In preferred embodiments: the first strand is DNA; the second strand is DNA.

In preferred embodiments: a mismatch is generated by a point mutation in the first strand or in the second strand; a mismatch is generated by a gross aberration in the first strand or in the second strand; a mismatch is generated by a deletion in the first strand or in the second strand; a mismatch is generated by an insertion in the first strand or in the second strand; the mismatch cleaved by the first or second resolvase is in any gene. For example, the mismatch can be in a gene which conditions cell proliferation, e.g., an oncogene, in a gene responsible for a congenital disorder, in a gene responsible for cell cycle regulation, or in a tumor suppressor gene. In another preferred embodiment, the mismatch can be in an extragenic region. In further preferred embodiments: the mismatch can be in one of the following genes: CFTR, APC, p53, Rb, BRCA1, HMSH1, or HMLH1.

In preferred embodiment, the method includes: (i) amplifying all or a portion of the first strand; (ii) amplifying all or a portion of the second strand; (iii) forming a duplex between an amplification product of the first strand and an amplification product of the second strand.

In other preferred embodiments, the method includes: (i) amplifying all or a portion of the first strand; (ii) providing a plurality of the second strands; (iii) forming a duplex between an amplification product of the first strand and one of the second strands.

In another aspect, the invention features a reaction mixture, preferably an in vitro reaction mixture, used in a method of the invention.

In preferred embodiments the reaction mixture includes one or more of: a first purified mismatch cleavage enzyme, e.g., a first purified resolvase, a second purified mismatch cleavage enzyme, e.g., a second purified resolvase, and, optionally, a purified nucleic acid molecule. In preferred embodiments the nucleic acid is a primer; a purified human DNA; a control or reference DNA which will form a mismatch with a target DNA having a mutation in a preselected gene. In preferred embodiments, the reaction mixture further includes: a reaction solution suitable for performing a cleavage reaction with the first mismatch cleavage enzyme, e.g., the first resolvase; a reaction solution suitable for performing a cleavage reaction with the second mismatch cleavage enzyme, e.g., the second resolvase.

In preferred embodiments the reaction mixture includes: a first primer, and a second primer, the first and second primers defining a region which includes a potential mismatch site in a preselected gene.

In preferred embodiments the reaction mixture includes: a human DNA, a first primer, and a second primer, the first and second primers.

In preferred embodiments the reaction mixture includes: a human DNA, a first primer, and a second primer, the first and second primers defining a region which includes potential mismatch site in a preselected gene and wherein the human DNA is wild-type at least one nucleotide in the region between said first and second primers.

In preferred embodiments one resolvase is T4E7 and the other is T7E1.

In another aspect, the invention features a kit for evaluating a nucleic acid. The kit includes one or more of the following components: a first purified mismatch cleavage enzyme, e.g., a first purified resolvase; a second purified mismatch cleavage enzyme, e.g., a second purified resolvase; a purified nucleic acid molecule, e.g., a primer, or a human DNA, or reference DNA used to form a duplex with a target DNA from the subject or sample; a reaction solution suitable for performing a cleavage reaction with the first mismatch cleavage enzyme, e.g., the first resolvase; a reaction solution suitable for performing a cleavage reaction with the second mismatch cleavage enzyme, e.g., the second resolvase; instructions for using the materials of the kit to test a subject or sample for the presence of a lesion.

In preferred embodiments the kit includes: a first primer, and a second primer, the first and second primers defining a region which includes a potential mismatch site in a preselected gene.

In preferred embodiments the kit includes: a human DNA, a first primer, and a second primer, the first and second primers.

In preferred embodiments the kit includes: a human DNA, a first primer, and a second primer, the first and second primers defining a region which includes potential mismatch site in a preselected gene and wherein the human DNA is wild-type at least one nucleotide in the region between said first and second primers.

In preferred embodiments one resolvase is T4E7 and the other is T7E1.

In preferred embodiments the kit includes a precast gel suitable for the analysis of nucleic acid samples.

Mismatch cleavage enzyme, as used herein, refers to an enzyme that cleaves a nucleic acid as the result of the presence of a distortion in a duplex.

Resolvase, as used herein, refers to an enzyme that cleaves a nucleic acid as the result of the presence of a distortion in a duplex, e.g., a bend, kink or other DNA deviation, e.g., a DNA mismatch, e.g., a single base pair substitution, insertion or deletion, in many different organisms, including bacteria, phage, yeast, and mammals, e.g., humans. The enzyme exerts its effect, usually cleavage of at least one DNA strand, close to the site of DNA distortion, e.g., a DNA mismatch. In preferred embodiments, the resolvase is isolated from a bacteriophage, e.g., bacteriophage T3, T4 or T7, and is selected from the group of resolvases consisting of T3E1, T4E7, or T7E1.

Amplify, as used herein, refers to any method which can be used to provide multiple copies of a nucleic acid, e.g., a DNA duplex or single strand DNA, its compliment, or both. Amplification techniques, therefore, include both cloning techniques, as well as, PCR based amplification techniques.

Duplex, as used herein, refers to a double stranded nucleic acid structure and includes perfectly matched duplexes, as well as, duplexes that contain one or more mismatches. Complimentary strand, as used herein, refers to a strand that is not only perfectly matched but also to a strand which when hybridized to a first strand exhibits one or more mismatches.

Mismatch, as used herein, refers to a duplex in which one or more of the following is present: (1) DNA nucleotide pairing other than A-T or G-C occurs, e.g., nucleotide paring such as A-C, A-G, A-A, T-C, T-G, T-T, G-G, or C-C occurs; (2) a deletion or insertion of one or more DNA nucleotides on one strand as compared to the other complimentary strand occurs, e.g., a deletion of 1, 2, 5, 10, 15, or more nucleotides or an insertion of 1, 2, 5, 10, 15, or more nucleotides occurs. DNA mismatches may arise from DNA replication errors, mutagenesis, deamination of 5-methylcytosine, and DNA recombination.

Mismatch-dependent cleavage, as used herein, refers to a characteristic of an enzyme, e.g., a resolvase. An enzyme has a mismatch-dependent cleavage activity if it cleaves at a mismatch, at a significantly higher rate, than it would cleave a corresponding perfectly matched sequence. In preferred embodiments, an enzyme with a mismatch-dependent cleavage is at least about 5%, 15%, 25%, 50%, 75% or 100% more efficient at cleaving at a mismatch than at a corresponding perfectly matched sequence.

Purification of Enzymes

To simplify isolation of the T4E7 and T7E1 resolvases, the two enzymes were linked to a polyhistidine sequence, permitting a one step purification by affinity column chromatography. DNA encoding T4E7 and T7E1 was amplified by the polymerase chain reaction (PCR) from total phage DNA. The PCR products were ligated into the bacterial expression vector pQiex12, in which the DNA inserts are expressed under the control of an IPTG-inducible promoter. This vector encodes a six histidine tag, which is appended to the C-terminus of the protein produced from it. After induction of *E. coli* transfected with the vector, tagged T4E7 and T7E1 were purified from bacterial extracts by binding and elution from a Ni-Sepharose column. Electrophoresis of the column eluate through an SDS-15% polyacrylamide gel indicate that the histidine-tagged enzymes purified by the single chromatography step were virtually homogeneous. An enzyme unit was arbitrarily defined as the amount of enzyme required to cleave 10% of 5 pmoles of a specific 15mer oligonucleotide heteroduplex in one hour at 37° C. Using this definition, the preparations of T4E7 and T7E1 had a specific activities of 550 and 31,500 units $mg^{-1}$, respectively.

Purification of T4E7 and T7E1 was performed as follows. DNA from the coding region of T4E7 and T7E1 was amplified by the PCR from T4 and T7 DNA, respectively. Primers used were (5' to 3') GGGGATCCATGTTAT-TGACTGGCAAATTATAC (SEQ ID NO:1) and GGAGATCTTTTGAGACTCTTTCTAAGCTGC (SEQ ID NO:2) for T4E7 and CCCGGATTCGCAGGTTACG-GCGCTAAAGG (SEQ ID NO:3) and CCCA-GATCTTTTCTTTCCTCCTTTCCT (SEQ ID NO:4) for T7E1. Amplification was carried out using cycling parameters of 94° C. for 10 seconds (denaturation), 55° C. for 30 seconds (annealing), and 72° C. for 30 seconds (primer extension) for 25 cycles. The PCR products were then digested with BamHI and Bgl II restriction enzymes and ligated into the pQiex12 expression plasmid (QiaGen, Chatsworth, Calif.). *E. coli* strain M15 (Villarejo and Zabin (1974) *J Bacteriol.* 120, 466–474) was transformed with the ligated vectors using the calcium chloride method. Expression of the protein from the vector was induced by addition of 0.1 mM IPTG to liquid cultures for 1 hour at 37° C. Bacterial extracts were prepared by sonication in a saline buffer, and histidine-tagged protein was purified over a Ni-Sepharose column (QiaGen, Chatsworth, Calif.) using elution with imidazole, all according to the manufacturer's instructions. Purity of the eluates from the columns was checked by SDS-polyacrylamide gel electrophoresis. Proteins were quantified by a Bradford assay (BioRad, Redmond, Calif.). Enzymes were stored in 50% glycerol, 10 mM Tris (pH 8.0), 0.1 mM glutathione, as previously described (Kosak and Kemper (1990) *Eur. JU. Biochem.* 194, 779–784) at −20° C. for up to six months without loss of activity.

Determination of unit activity was determined as follows. The sequence of the two complementary oligonucleotides used to determine unit activity were (5' to 3') GATCCGTC GACCTGC (SEQ ID NO:5) and GCAGGTTGACGGATC (SEQ ID NO:6) (Don et al. (1991) *Nucl. Acids Res.* 19, 4008), where the mismatched bases have been underlined. The first oligonucleotide was 5' end labeled with $^{32}$P-γ-ATP and T4 polynucleotide kinase (NE Biolabs, Beverly, Mass.) and added to an equimolar amount of the second primer. Five pmoles of the heteroduplex were mixed with varying concentrations of the two enzymes using the reaction conditions described below. Reaction products were analyzed by autoradiography after electrophoresis through a 20% polyacrylamide gel. Autoradiogram optical density was measured with a scanning densitometer (EC Apparatus Model 910, St. Petersburg, Fla.) using GS365W Electorphoresis Data System software (Hoeffer Scientific, San Francisco, Calif.).

Substrates Analyzed

Both resolvases were tested on a variety of mutations. Genomic DNA was isolated from normal cells or cells known to be heterozygous for mutations within one of three genes: familial adenomatous polyposis coli (APC); p53; and the cystic fibrosis transmembrane receptor (CFTR). In one case, the E1408X mutation of the APC gene, the DNA was derived from a hemizygous colonic adenoma, in which one copy of the gene had been deleted, leaving only a mutant allele. Since the starting material for this case, as well as several others with APC mutations, consisted of histologic sections of formalin-fixed, paraffin embedded tissues, sufficient substrate for analysis generally required two successive rounds of amplification. These two rounds of amplification were composed of 35 and 20 cycles of PCR. To maintain uniformity in substrate preparation, DNA from other samples, even those for which more tissue was available, were amplified in a similar manner. This extensive degree of amplification also served to exclude Taq polymerase error as a potentially complicating variable in the analyses. In the case of the E1408X mutation, equimolar amounts of wild type and mutant PCR products were mixed before the second round of amplification.

Following the final cycle of PCR, the DNA was heat-denatured and allowed to reanneal before subsequent purification by electrophoresis through a low melting point agarose gel. PCR products were recovered from the agarose gel slices and used directly in the resolvase assay. The last denaturation and reannealing step prior to gel electrophoresis was introduced to disrupt homoduplexes formed during the final PCR cycle. Purification of duplexes by gel electrophoresis was found to reduce background cleavage in denaturing gels presumably due to cutting of improperly paired strands.

The various heteroduplexes assayed contained deletions of one to three nucleotides in one strand and at least one example of point mutations representing each of the four different possible classes of single nucleotide mismatches between the strands (Table 1). The length of these heteroduplex fragments ranged from 88 base pairs (bp) to 940 bp.

TABLE 1

Heteroduplex mismatches resulting from point mutations.

| Mutation | Mismatches |
|---|---|
| G → A | |
| A → G | A/C |
| C → T | + |
| T → C | G/T |
| C → A | |
| A → C | A/G |
| T → G | + |
| G → T | T/C |
| G → C | G/G |
| | + |
| C → G | C/C |
| A → T | A/A |
| | + |
| T → A | T/T |

The 12 possible single base mutations are displayed on the left, and the four possible classes of mismatches which result from those base changes in double-stranded heteroduplexes are shown at the right.

The specific mutations analyzed and the primers used for PCR amplification of DNA containing these mutations are shown in the table below (Table 2).

TABLE 2

| Gene | Mutant Size (bp) | Base change (sense strand) | PCR Primers (5' → 3') | Size (bp) | Predicted Fragment Sizes | Observed Fragment Sizes T4E7 | Observed Fragment Sizes T7E1 |
|---|---|---|---|---|---|---|---|
| APC | K670X | A → T | GTTACTGCATACACATTGTGAC (SEQ ID NO:7) | 372 | 268 | 265 | ND |
| | | | GCTTTTTGTTTCCTAACATGAAG (SEQ ID NO:8) | | 104 | 105 | |
| | ΔP1443 | CCT → CC | ATCTCCCTCCAAAAGTGGTGC (SEQ ID NO:9) | 420 | 252 | 256 | 250 |
| | | | TCCATCTGGAGTACTTTCTGTG (SEQ ID NO:10) | | 168 | 170 | 164 |
| | R1450X | C → T | | | 272 | ND | 260 |
| | | | | | 148 | | 146 |
| | E1408X | G → T | | | 276 | 283 | 278 |
| | | | | | 144 | 143 | 139 |
| P53 | R196P | G → C | TCCCCAGGCCTCTGATTCCT (SEQ ID NO:11) | 940 | 877 | _880 | _870 |
| | | | | | 63 | OG | OG |
| | G245C | G → T | GAGGTGGATGGGTAGTAG (SEQ ID NO:12) | | 776 | _785 | _770 |
| | | | | | 164 | _166 | _160 |
| | G245S | G → A | | | 776 | _785 | ND |
| | | | | | 164 | _166 | |
| | R196Q | G → A | | | 877 | ND | _870 |
| | | | | | 63 | | OG |
| CFTR | 1717-1 | G → A | GTTAAAGCAATAGTGTGATATATGAT (SEQ ID NO:13) | 418 | 310 | 314 | 308 |
| | Exon 11/12 splice | | CACAGATTCTGAGTAACCATAAT (SEQ ID NO:14) | | 108 | 111 | 109 |
| | R560T | G → C | | | 217 | 234 | 228 |
| | | | | | 201 | 207 | 200 |
| | G551D | G → A | | | 243 | ND | ND |
| | | | | | 175 | | |
| | G542X | G → T | | | 271 | 276 | 271 |
| | | | | | 147 | 152 | 144 |
| | 621+1 | G → T | CTTCCTATGACCCGGATAACA (SEQ ID NO:15) | 250 | 171 | 174 | 169 |
| | Exon 4/5 splice | | GCTCACTACCTAATTTATGACA (SEQ ID NO:16) | | 79 | 80 | 73 |
| | W1282X | G → A | TCACTTTTACCTTATAGGTGGGC (SEQ ID NO:17) | 197 | 138 | 143 | 138 |
| | | | TTCTGGCTAAGTCCTTTTGCTCA (SEQ ID NO:18) | | 59 | 60 | 55 |
| | N1303K | C → G | AGGGACTCCAAATATTGCTGT (SEQ ID NO:19) | 280 | 255 | 261 | 255 |
| | | | CACTCCACTGTTCATAGGGATCTAA (SEQ ID NO:20) | | 25 | OG | OG |
| | ΔI507 | CATC → C | GTTTTCCTGGATTATGCCTGGCAC (SEQ ID NO:21) | 88 | 55 | 57 | 54 |
| | | | GTTGGCATGCTTTGATGACGCTTC (SEQ ID NO:22) | | 33 | 37 | 33 |
| | ΔF508 | TCTT → T | | | 52 | 57 | 52 |
| | | | | | 36 | 37 | 33 |

Preparation of DNA for analysis was performed as follows. DNA from fresh or frozen tissues isolated using conventional phenol-chloroform extraction and precipitation in cold ethanol. DNA from paraffin-embedded tissues, prepared by dissecting tumor tissue from histologic sections, boiling in 50 mM Tris pH 8.0, 1% SDS in the presence of Chelex-100 (Sigma, St. Louis, Mo.) or by proteinase-K digestion, phenol-chloroform extraction, and ethanol precipitation. DNA was amplified from genomic DNA for 35 cycles of PCR. In all cases except for the codon 1408 mutation of the APC gene, the DNA amplified was heterozygous for the mutation studied. For the initial amplification, a touchdown protocol (Jirieny, et al. (1988) Nucl. Acids Res. 16, 7843–7853) was employed, beginning at 6° C. above the predicted melting temperature of the primers at 94° C. for 10 seconds, annealing temperature for 30 seconds, and 72° C. for thirty seconds. Ten cycles of touchdown with a 1° C. decrease in annealing temperature per cycle were followed by 25 cycles at 4° C. below the predicted melting temperature of the primers. 2.5 µl of the initial reaction was then reamplified for a further 20 cycles of PCR at an annealing temperature 4° C. below the predicted melting temperature of the primers in a reaction volume of 100 µl. This second round of PCR was optional when more abundant genomic DNA was available as starting material. In the case of the APC codon 1408 mutation, equimolar amounts of wild type and mutant PCR product were mixed prior to reamplification. The reaction products were fractionated by electrophoresis in a low melting point (LMP) agarose gel and visualized after staining with ethidium bromide. The predominant band was excised from the gel and DNA fragments were then isolated by digestion of the gel slice with β-agarase (NE BioLabs, Beverly, Mass.), according to the manufacturer's instructions. About 0.05 pmoles of PCR product were 5' end-labeled with $^{32}$P-γ-ATP and T4 polynucleotide kinase. Following the incubation, ATP was removed by separation over a Sepharose G-50 spin column.

Alternatively, PCR products were labeled during a single round of amplification using primers which had been 5' end-labeled with $^{32}$P-γ-ATP and T4 polynucleotide kinase prior to PCR.

Digestion with T4E7 and T7E1 was performed as follows. Approximately 5 fmoles of labeled DNA were added to reaction mixtures containing 50 mM Tris (pH8.0), 50 mM potassium glutamate, 10 mM magnesium chloride, 10 μg ml$^{-1}$ sonicated salmon sperm DNA, 5 mM dithiothreitol, 5% glycerol, and 50 ng (0.0275 unit) of T4E7 or 80 ng (2.5 units) of T7E1 in a reaction volume of 10 μl. The reaction mixtures were incubated at 37° C. for 30 minutes. In the case of T7E1, reactions also contained 7.5% dimethylsulfoxide. Reactions were stopped by addition of 5 μl of loading buffer containing 20 mM EDTA, 25% glycerol, and 20 mM Tris pH 8.0 for non-denaturing gels, or 20 mM EDTA and 95% formamide for denaturing gels. DNA fragments were heat-denatured at 85° C. prior to application to the denaturing gels. Electrophoresis was performed in an 8% polyacrylamide gel with Tris-borate-EDTA buffer at 8 V cm$^{-1}$ at 4° C. or in a 6% polyacrylamide gel containing 7.2M urea in Tris-borate-EDTA buffer at 60 W. Gels were transferred to filter paper, dried, and exposed to autoradiographic film for 18–42 hours.

Optimization of Reaction Conditions

DNA substrate was 5' end-labeled using T4 polynucleotide kinase and γ-$^{32}$P-ATP. Both strands of DNA fragment are expected to be labeled by this procedure. Excess ATP was removed, and the DNA substrate incubated with resolvase. The DNA was then subjected to polyacrylamide gel electrophoresis, and the reaction products visualized by autoradiography of the gel.

Reaction conditions were optimized on the 621+1 mutation at the exon 4/5 splice site of CFTR and the R196Q mutation of p53 for the following variables: the concentration of resolvase, of Na$^+$, K$^+$, and Mg$^{+2}$ cations, and of salmon sperm DNA; the presence and concentration of urea, formamide, ethylene glycol, ethidium bromide, dimethylsulfoxide; the use of Mg$^{+2}$, Mn$^{+2}$, or Ca$^{+2}$ as the divalent cation; the use of glutamate or chloride as the anion; pH; and temperature. Optimal conditions determined and used in all later studies were those described herein. In general, inclusion of K$^+$ and glutamate increased the specific cleavage. Addition of dimethylsulfoxide slightly improved cleavage by T7E1 but inhibited cleavage by T4E7. The temperature of the reaction made little difference over a range from 16°–37° C.; however, minimal cleavage was observed at 4° C. and increased non-specific cleavage was observed at 42° C.

Enzymatic Cleavage Analysis

Cleavage of DNA fragments was indicated by the production of relatively more intense bands against a background of non-specific bands in the autoradiograms of polyacrylamide gels. These background bands were usually fainter than the specific bands and appeared in identical positions in analyses of wild type fragments and mutant fragments. Deletions were cleaved more efficiently than point mutations, based on the presence of more intense bands in analyses of the former. The predicted and observed sizes of the fragments resulting from enzyme cleavage are summarized in Table 2.

Most mutations were recognized by both enzymes, but some were recognized much more efficiently by one or the other resolvase. For example, the APC K670X mutation was detected only by T4E7, while the R1450X mutation was detected only by T7E1. A single point mutation, the G551D mutation in exon 11 of the CFTR gene, among the 14 point mutations tested was not recognized by either enzyme in a 408 bp fragment. The same mutation was also not detected in a smaller PCR product consisting of 295 bp derived from one end of the original fragment. Use of both enzymes together in a single reaction was inferior to the use of the two enzymes separately. Fewer background bands were seen when the reaction products were fractionated by electrophoresis under non-denaturing conditions as compared to denaturing conditions, apparently because of single-stranded nicks generated by the resolvases or contaminating enzyme activities. However, the presence of background bands in analyses using non-denaturing gel electrophoresis indicates that cleavages at both specific and non-specific sites occur in both strands of the heteroduplex. When large PCR fragments were analyzed under non-denaturing conditions, some mutations easily detected under denaturing conditions were not easily identified, possibly due to failure of the resolvases to cut both strands of the DNA.

Most of the studies reported herein were performed on fragments labeled with $^{32}$P-γ-ATP and T4 polynucleotide kinase after PCR amplification. For two mutations, the P1443 mutation of the APC gene, and the R196Q mutation of the p53 gene, the assay was performed directly on the products of a single round of PCR amplification using $^{32}$P end-labeled primers, followed directly by electrophoresis on a non-denaturing gel. The results obtained with fragments labeled in this fashion and without subsequent gel purification were similar to those generated with gel-purified fragments labeled after PCR.

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

GGGGATCCAT GTTATTGACT GGCAAATTAT AC                                         32

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

GGAGATCTTT TGAGACTCTT TCTAAGCTGC                                            30

( 2 ) INFORMATION FOR SEQ ID NO:3:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

CCCGGATTCG CAGGTTACGG CGCTAAAGG                                             29

( 2 ) INFORMATION FOR SEQ ID NO:4:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

CCCAGATCTT TTCTTTCCTC CTTTCCT                                               27

( 2 ) INFORMATION FOR SEQ ID NO:5:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

GATCCGTCGA CCTGC                                                            15

( 2 ) INFORMATION FOR SEQ ID NO:6:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

GCAGGTTGAC GGATC                                                            15

( 2 ) INFORMATION FOR SEQ ID NO:7:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

GTTACTGCAT ACACATTGTG AC        22

( 2 ) INFORMATION FOR SEQ ID NO:8:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

GCTTTTTGTT TCCTAACATG AAG        23

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

ATCTCCCTCC AAAAGTGGTG C        21

( 2 ) INFORMATION FOR SEQ ID NO:10:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

TCCATCTGGA GTACTTTCTG TG        22

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

TCCCCAGGCC TCTGATTCCT        20

( 2 ) INFORMATION FOR SEQ ID NO:12:

( i ) SEQUENCE CHARACTERISTICS:
        ( A ) LENGTH: 18 base pairs (B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:12:

GAGGTGGATG GGTAGTAG 18

(2) INFORMATION FOR SEQ ID NO:13:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:13:

GTTAAAGCAA TAGTGTGATA TATGAT 26

(2) INFORMATION FOR SEQ ID NO:14:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:14:

CACAGATTCT GAGTAACCAT AAT 23

(2) INFORMATION FOR SEQ ID NO:15:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:15:

CTTCCTATGA CCCGGATAAC A 21

(2) INFORMATION FOR SEQ ID NO:16:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:16:

GCTCACTACC TAATTTATGA CA 22

(2) INFORMATION FOR SEQ ID NO:17:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA ( x i ) SEQUENCE DESCRIPTION: SEQ ID NO:17:

TCACTTTTAC CTTATAGGTG GGC 23

( 2 ) INFORMATION FOR SEQ ID NO:18:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:18:

TTCTGGCTAA GTCCTTTTGC TCA 23

( 2 ) INFORMATION FOR SEQ ID NO:19:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:19:

AGGGACTCCA AATATTGCTG T 21

( 2 ) INFORMATION FOR SEQ ID NO:20:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:20:

CACTCCACTG TTCATAGGGA TCTAA 25

( 2 ) INFORMATION FOR SEQ ID NO:21:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:21:

GTTTTCCTGG ATTATGCCTG GCAC 24

( 2 ) INFORMATION FOR SEQ ID NO:22:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:22:

GTTGGCATGC TTTGATGACG CTTC 24

Other embodiments are within the following claims.

What is claimed is:

1. A method of detecting a mismatch between a first nucleic acid strand and a second nucleic acid strand comprising:

forming a plurality of duplexes, each duplex including a molecule of said first nucleic acid strand, or a portion thereof, and a molecule of said second nucleic acid strand, or a portion thereof;

contacting a first bacteriophage resolvase and a second bacteriophage resolvase with said plurality of duplexes, wherein said first and said second resolvases are different;

determining if said plurality of duplexes is cleaved by either or both of said first and said second resolvases, wherein cleavage indicates the presence of a mismatch.

2. The method of claim 1, wherein said first strand is derived from a subject at risk for a mutation and the second strand has a wild-type sequence for said mutation.

3. The method of claim 2, wherein said second strand is derived from the subject at risk for a mutation.

4. The method of claim 2, wherein said second strand is derived from a subject not at risk for a mutation or for a disorder associated with a mutation.

5. The method of claim 1, wherein said first bacteriophage resolvase is bacteriophage T4 endonuclease VII.

6. The method of claim 1, wherein said second bacteriophage resolvase is bacteriophage T7 endonuclease I.

7. The method of claim 1, wherein said first bacteriophage resolvase and said second bacteriophage resolvase cleave at a particular mismatch with different efficiencies.

8. The method of claim 1, wherein said first and second strands are DNA.

9. The method of claim 1, wherein said mismatch is generated by a point mutation in the first strand or in the second strand.

10. The method of claim 1, wherein said mismatch is in one of the following genes: CFTR, APC, p53, Rb, BRCA1, HMSH1, or HMLH1.

11. A method of detecting a mismatch between a first nucleic acid strand and a second nucleic acid strand comprising:

amplifying a portion of said first strand;

providing a plurality of said second strands;

forming a first duplex between an amplification product of said first strand and one of said second strands;

forming a second duplex between an amplification product of said first strand and one of said second strands;

contacting said first duplex with a first bacteriophage resolvase;

contacting said second duplex with a second bacteriophage resolvase, wherein said first and said second resolvases are different;

determining if at least one strand of said duplex is cleaved, cleavage being indicative of a mismatch.

12. A method of determining the location of a mismatch between a first nucleic acid strand and a second nucleic acid strand comprising:

forming a plurality of duplexes, each duplex including a molecule of said first nucleic acid strand, or a portion thereof, and a molecule of said second nucleic acid strand, or a portion thereof;

contacting a first bacteriophage resolvase and a second bacteriophage resolvase with said plurality of duplexes, wherein said first and said second resolvases are different;

determining the distance between the cleavage site and a second site on the strand (or the complement of the strand).

13. A method of determining the location of a mismatch between a first nucleic acid strand and a second nucleic acid strand comprising:

forming a first duplex between a molecule of said first strand, or a portion thereof, and a molecule of said second strand, or a portion thereof;

contacting said first duplex with a first bacteriophage resolvase;

forming a second duplex between a molecule of said first strand and a molecule of said second strand;

contacting said second duplex with a second bacteriophage resolvase wherein said first and said second resolvases are different;

determining the distance between the cleavage site and a second site on the strand (or the complement of the strand) by determining the size of a cleavage product, thereby determining the location of said mismatch.

14. The method of claim 13, wherein said first resolvase is contacted with said first duplex in a first reaction mixture and said second resolvase is contacted with said second duplex in a second reaction mixture.

15. The method of claim 13, wherein said first strand is derived from a subject at risk for a mutation and the second strand has a wild-type sequence for said mutation.

16. The method of claim 15, wherein said second strand is derived from the subject at risk for a mutation.

17. The method of claim 15, wherein said second strand is derived from a subject not at risk for a mutation or for a disorder associated with a mutation.

18. The method of claim 13, wherein said first bacteriophage resolvase is bacteriophage T4 endonuclease VII.

19. The method of claim 13, wherein said second bacteriophage resolvase is bacteriophage T7 endonuclease I.

20. The method of claim 13, wherein said first bacteriophage resolvase and said second bacteriophage resolvase cleave at a particular mismatch with different efficiencies.

21. The method of claim 13, wherein said first and second strands are DNA.

22. The method of claim 13, wherein said mismatch is generated by a point mutation in the first strand or in the second strand.

23. The method of claim 13, wherein said mismatch is in one of the following genes: CFTR, APC, p53, Rb, BRCA1, HMSH1, or HMLH1.

24. An in vitro reaction mixture comprising: a first purified bacteriophage resolvase;

a second purified bacteriophage resolvase, wherein said first and said second resolvases are different; and a purified nucleic acid molecule.

25. A kit comprising: a first purified bacteriophage resolvase; a second purified bacteriophage resolvase, wherein said first and said second resolvases are different; and a purified nucleic acid molecule.

26. The method of claim 1, wherein said bacteriophage resolvases are purified resolvases.

27. The method of claim 1, wherein said first nucleic acid strand is human DNA.

28. The method of claim 1, wherein said first and said second bacteriophage resolvases are in two separate reaction mixtures.

29. The method claim 1, further comprising providing a plurality of said first strands.

30. The method of claim 1, further comprising providing a plurality of said second strands.

* * * * *